United States Patent
Li et al.

(10) Patent No.: US 11,806,192 B2
(45) Date of Patent: Nov. 7, 2023

(54) GUIDING SYSTEM AND GUIDING METHOD FOR ULTRASOUND SCANNING OPERATION

(71) Applicant: Industrial Technology Research Institute, Hsinchu (TW)

(72) Inventors: Chien-Ju Li, Hsinchu County (TW); Peng-Zhi Sun, Hsinchu (TW); Yi-Jung Wang, Hsinchu County (TW); Brian Hsu, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 80 days.

(21) Appl. No.: 17/510,373

(22) Filed: Oct. 25, 2021

(65) Prior Publication Data
US 2022/0175347 A1 Jun. 9, 2022

Related U.S. Application Data

(60) Provisional application No. 63/122,955, filed on Dec. 9, 2020.

(30) Foreign Application Priority Data

Jun. 21, 2021 (TW) ................................. 110122601

(51) Int. Cl.
*A61B 8/00* (2006.01)
(52) U.S. Cl.
CPC .............. *A61B 8/46* (2013.01); *A61B 8/4254* (2013.01); *A61B 8/565* (2013.01); *A61B 8/44* (2013.01); *A61B 8/4472* (2013.01)
(58) Field of Classification Search
CPC ......... A61B 8/46; A61B 8/4254; A61B 8/565; A61B 8/44; A61B 8/4472
See application file for complete search history.

(56) References Cited

U.S. PATENT DOCUMENTS

| 3,005,691 A1 | 8/2011 | Kumar et al. |
| 9,021,358 B2 | 4/2015 | Amble et al. |

(Continued)

FOREIGN PATENT DOCUMENTS

| CN | 107049497 | 8/2017 |
| CN | 109567865 | 4/2019 |

(Continued)

OTHER PUBLICATIONS

Rajesh Kannan Megalingam et al., "PULSS: Portable Ultrasound Scanning System", IEEE Global Humanitarian Technology Conference: South Asia Satellite (GHTC-SAS), Aug. 2013, pp. 119-123.

(Continued)

*Primary Examiner* — Katherine L Fernandez
*Assistant Examiner* — Brooke Lyn Klein
(74) *Attorney, Agent, or Firm* — JCIPRNET

(57) ABSTRACT

A guiding system and a guiding method for ultrasound scanning operation are provided. The guiding system includes a handheld guiding device, a display device, an ultrasound scanning device, a prompting device, and a control host. When the handheld guiding device generates a first physical motion, the control host detects the first physical motion and generates navigation prompting information accordingly. The prompting device is suitable for presenting the navigation prompting information to guide the ultrasound scanning device to move to generate a second physical motion. The control host captures an ultrasound image via the ultrasound scanning device and sends the ultrasound image to the display device at a guiding end for display.

12 Claims, 6 Drawing Sheets

(56) References Cited

U.S. PATENT DOCUMENTS

| | | | |
|---|---|---|---|
| 10,220,172 B2 | 3/2019 | Lucey et al. | |
| 2013/0053697 A1* | 2/2013 | Holl | A61B 8/4472 |
| | | | 600/459 |
| 2013/0237811 A1 | 9/2013 | Mihailescu et al. | |
| 2013/0338447 A1 | 12/2013 | Gilad-Gilor | |
| 2015/0335315 A1* | 11/2015 | Choi | A61B 8/462 |
| | | | 600/437 |
| 2016/0317122 A1* | 11/2016 | sos Santos Mendonca | |
| | | | A61B 8/54 |
| 2017/0105701 A1 | 4/2017 | Pelissier et al. | |
| 2017/0273601 A1 | 9/2017 | Wang et al. | |
| 2017/0360403 A1 | 12/2017 | Rothberg et al. | |
| 2018/0132724 A1* | 5/2018 | Waechter-Stehle | A61B 34/30 |
| 2019/0059851 A1* | 2/2019 | Rothberg | A61B 8/42 |
| 2022/0071593 A1* | 3/2022 | Tran | A61B 8/4444 |

FOREIGN PATENT DOCUMENTS

| | | |
|---|---|---|
| JP | H06327681 | 11/1994 |
| JP | 2006115986 | 5/2006 |
| JP | 2015217306 | 12/2015 |
| TW | I669681 | 8/2019 |
| TW | 201936114 | 9/2019 |
| WO | 2015016247 | 2/2015 |
| WO | 2020082181 | 4/2020 |

OTHER PUBLICATIONS

M. Solano et al., "Asynchronous Telemedicine with Ultrasound: Improving Maternal Health in Developing Countries", 2009 IEEE International Ultrasonics Symposium Proceedings, Sep. 2009, pp. 2316-2319.

R Bharath et al., "Subjective Liver Ultrasound Video Quality Assessment of Internet based Videophone Services for Real-Time Telesonography", 2017 IEEE 19th International Conference on e-Health Networking, Applications and Services (Healthcom), Oct. 2017, pp. 1-6.

"Office Action of Japan Counterpart Application", dated Dec. 6, 2022, p. 1-p. 3.

"Office Action of Taiwan Counterpart Application", dated Mar. 22, 2022, p. 1-p. 6.

"Search Report of Europe Counterpart Application", dated Apr. 29, 2022, p. 1-p. 9.

"Notice of allowance of Japan Counterpart Application", dated Apr. 4, 2023, p. 1-p. 2.

* cited by examiner

GUIDING SYSTEM AND GUIDING METHOD FOR ULTRASOUND SCANNING OPERATION

CROSS-REFERENCE TO RELATED APPLICATION

This application claims the priority benefit of U.S. Provisional Application No. 63/122,955, filed on Dec. 9, 2020 and Taiwan application serial no. 110122601, filed on Jun. 21, 2021. The entirety of each of the above-mentioned patent applications is hereby incorporated by reference herein and made a part of this specification.

BACKGROUND

Technical Field

The disclosure relates to a guiding system and a guiding method for ultrasound scanning operation.

Description of Related Art

Ultrasound scanning technology may be applied to fetal examinations and examinations of human organs such as the heart. Generally speaking, the ultrasound scanning device must be operated by professionals such as doctors or examiners to perform ultrasound scanning of the body of a patient on site. However, in the application of telemedicine, doctors cannot contact the patient on site and also cannot operate the ultrasound scanning device on site, which makes it difficult to obtain ultrasound images of the remote patient.

SUMMARY

The disclosure provides a guiding system and a guiding method for ultrasound scanning operation, which can improve capturing efficiency of an ultrasound image in telemedicine.

The embodiment of the disclosure provides a guiding system for ultrasound scanning operation, which includes a handheld guiding device, a display device, an ultrasound scanning device, a prompting device, and a control host. The handheld guiding device is located at a guiding end. The display device is located at the guiding end. The ultrasound scanning device is located at an operating end. The prompting device is located at the operating end. The control host is communicatively connected to the guiding end and the operating end. When the handheld guiding device generates a first physical motion, the control host detects the first physical motion and generates navigation prompting information accordingly. The prompting device is suitable for presenting the navigation prompting information to guide the ultrasound scanning device to move to generate a second physical motion. The control host captures an ultrasound image via the ultrasound scanning device and sends the ultrasound image to the display device at the guiding end for display.

The embodiment of the disclosure also provides a guiding method for ultrasound scanning operation, which is executed by using the guiding system for ultrasound scanning operation. The guiding method includes the following steps. The first physical motion of the handheld guiding device is detected. The navigation prompting information is generated according to the first physical motion, and the navigation prompting information is presented via the prompting device. The ultrasound image is captured via the ultrasound scanning device. The ultrasound image is sent to the display device for display.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1:
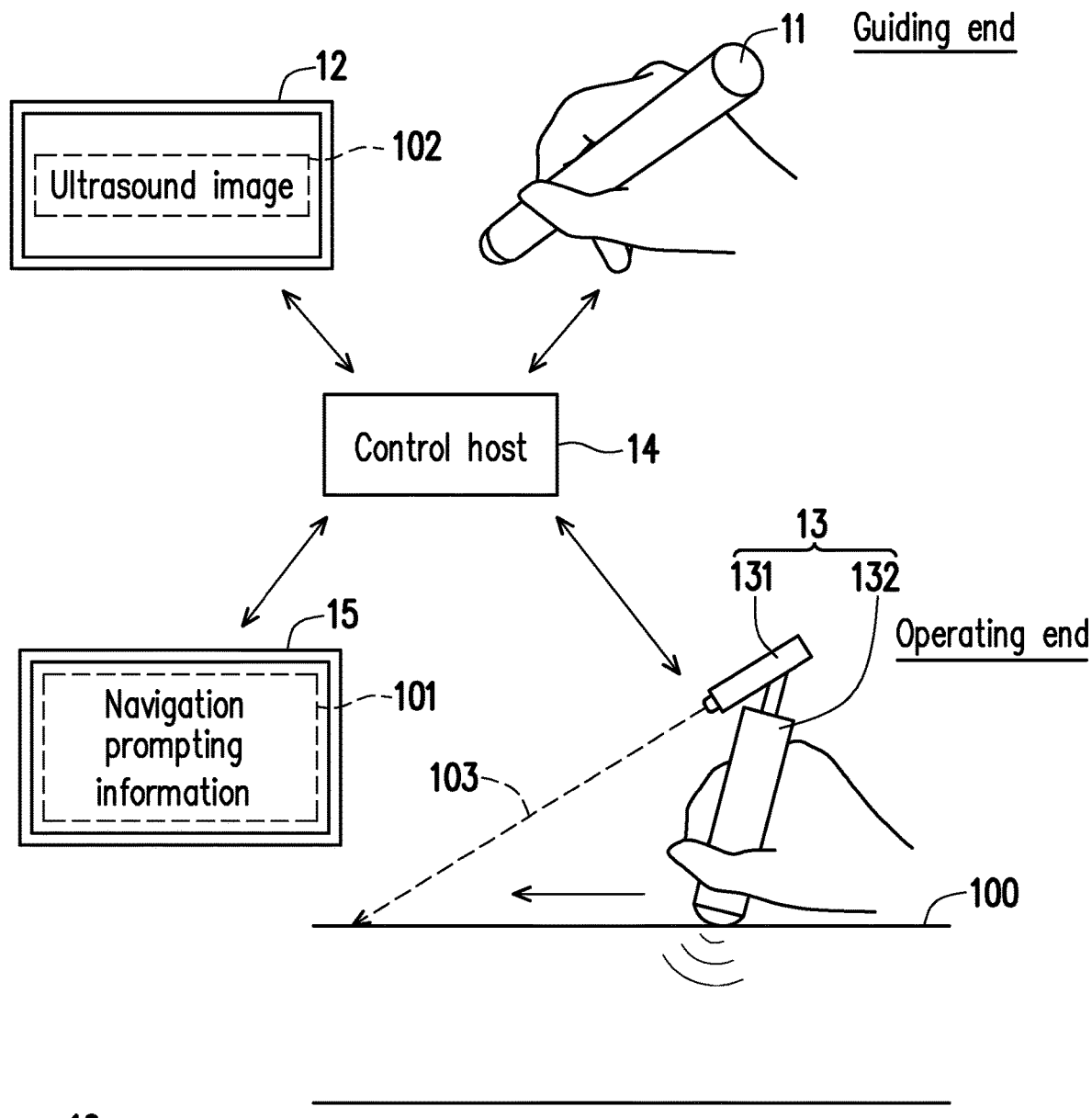
FIG. 1 is a schematic diagram of a guiding system for ultrasound scanning operation according to an embodiment of the disclosure.

FIG. 1 is a schematic diagram of a guiding system for ultrasound scanning operation according to an embodiment of the disclosure. Please refer to FIG. 1. A guiding system for ultrasound scanning operation 10 includes a handheld guiding device 11, a display device 12, an ultrasound scanning device 13, a control host 14, and a prompting device 15. The handheld guiding device 11 and the display device 12 are located at a guiding end. The ultrasound scanning device 13 and the prompting device 15 are located at an operating end. The control host 14 may be communicatively connected to the guiding end and the operating end.

The handheld guiding device 11 may be operated by a user to generate a first physical motion. The first physical motion is suitable for guiding the ultrasound scanning device 13 to move. In an embodiment, the handheld guiding device 11 includes a handheld control device such as a stylus pen or an electronic control stick. Alternatively, in an embodiment, the handheld guiding device 11 may include a handheld ultrasound scanner.

The display device 12 is suitable for displaying an image. For example, the display device 12 may include a display or a display device containing a display such as a notebook computer, a tablet computer, or a television. The handheld guiding device 11 and the display device 12 may be wired or wirelessly coupled to the control host 14 to communicate with the control host 14.

The ultrasound scanning device 13 is suitable for executing ultrasound scanning on a target 100. The target 100 is, for example, a human body. In an embodiment, the ultrasound scanning device 13 may include a handheld ultrasound scanner. In addition, the ultrasound scanning device 13 may be wired or wirelessly coupled to the control host 14 to communicate with the control host 14.

The control host 14 is suitable for sending information between the guiding end and the operating end and may execute functions such as data processing. For example, the control host 14 may include a computer device such as a notebook computer, a desktop computer, a tablet computer, an industrial computer, or a server. In addition, the number of the handheld guiding device 11, the display device 12, the ultrasound scanning device 13, and the control host 14 are not limited and may be one or more.

The prompting device 15 is suitable for presenting navigation prompting information from the control host 14 to guide the ultrasound scanning device 13 to move. In FIG. 1, the prompting device 15 is exemplified by a display. However, in another embodiment, the prompting device 15 may also include various signal or information output devices such as a sound-emitting device (such as a speaker or a buzzer) and/or a vibration device (such as a vibrator). The prompting device 15 may be independent of the ultrasound scanning device 13 or disposed on the ultrasound scanning device 13. In addition, the prompting device 15 may be wired or wirelessly coupled to the control host 14 to communicate with the control host 14.

When the handheld guiding device 11 generates the first physical motion, the control host 14 may detect the first physical motion of the handheld guiding device 11 located at the guiding end. In an embodiment, the first physical motion may include a motion executed in a physical space by the handheld guiding device 11 operated by a user, such as moving toward a certain direction, tilting toward a certain direction, and/or pressing toward a certain direction. The control host 14 may generate navigation prompting information 101 according to the first physical motion to be presented via the prompting device 15 located at the operating end. In an embodiment, the navigation prompting information 101 may guide the ultrasound scanning device 13 located at the operating end to execute a second physical motion correspondingly according to the first physical motion. During a process of the ultrasound scanning device 13 executing the second physical motion, the control host 14 may capture an ultrasound image 102 via the ultrasound scanning device 13. In an embodiment, the ultrasound image 102 may be obtained by the ultrasound scanning device 13 executing the second physical motion to perform ultrasound scanning on the target 100. The control host 14 may send the ultrasound image 102 to the display device 12 located at the guiding end for display.

In an embodiment, the user operating the handheld guiding device 11 at the guiding end is also referred to as an instructor, such as a doctor or an examiner who has been professionally trained in ultrasound scanning. In an embodiment, the user who operates the ultrasound scanning device 13 at the operating end is also referred to as an operator, such as medical staff or ordinary people who may not be professionally trained in ultrasound scanning.

In an embodiment, the instructor at the guiding end may view the ultrasound image 102 returned by the operating end via the display device 12. At the same time, the instructor may operate the handheld guiding device 11 to execute the first physical motion to guide the operator at the operating end to operate the ultrasound scanning device 13 to execute the second physical motion. In another embodiment, the instructor at the guiding end may first view environmental information provided by the operating end via the display device 12 to know the location of the ultrasound scanning device 13. In detail, the instructor at the guiding end may first provide a feature point for the operator at the operating end to first place the ultrasound scanning device 13 as a starting point for scanning. Taking the target 100 as a human abdomen as an example, when performing abdominal ultrasound scanning, the feature point may be set as a belly button of a human body. The operator at the operating end may place the ultrasound scanning device 13 at the location of the belly button, which is the feature point. Then, the instructor at the guiding end may view the environmental information of the location of the ultrasound scanning device 13 via the display device 12, thereby evaluating an operating direction of the first physical motion. During operation, the instructor uses the handheld guiding device 11 to execute the first physical motion to guide the operator to correspondingly execute the second physical motion. Through such interactive guiding operation, even if the operator at the operating end is not familiar with the usage manner of the ultrasound scanning device 13, the operator at the operating end may still capture a suitable ultrasound image from the target 100 according to the guidance of the instructor.

Figure 2:
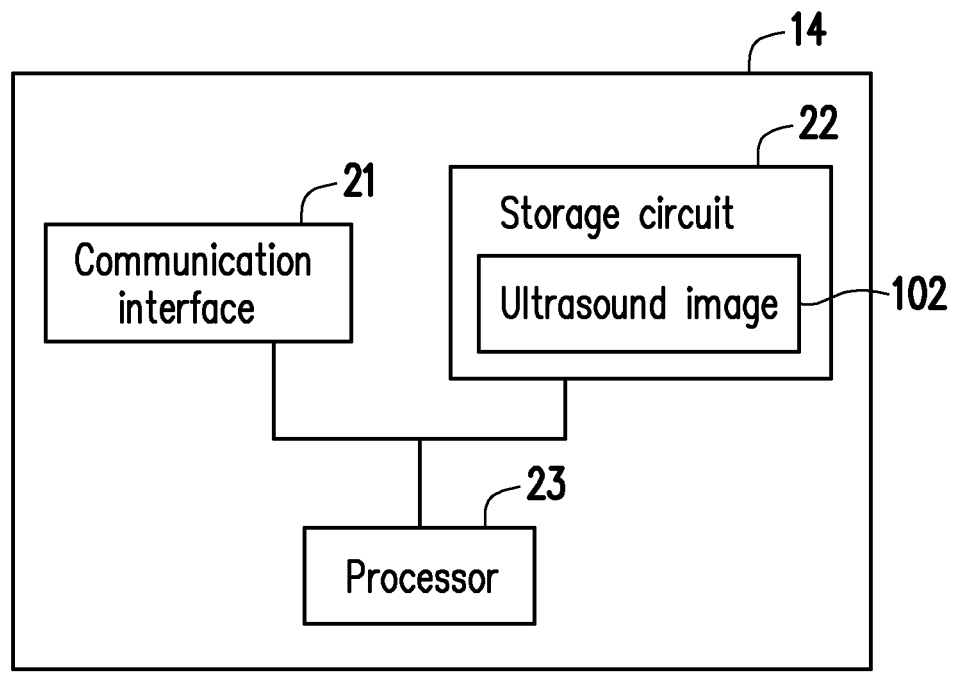
FIG. 2 is a schematic block diagram of a control host according to an embodiment of the disclosure.

FIG. 2 is a schematic block diagram of a control host according to an embodiment of the disclosure. Please refer to FIG. 2. The control host 14 may include a communication interface 21, a storage circuit 22, and a processor 23. The communication interface 21 may include a communication circuit (such as a wired and/or wireless network card). For example, the communication interface 21 may support wireless communication protocols such as Wi-Fi, Bluetooth, Bluetooth Low Energy (BLE), or long-term evolution (LTE), or wired communication protocols such as Ethernet.

The storage circuit 22 is suitable for storing data. For example, the storage circuit 22 may include a volatile storage circuit and a non-volatile storage circuit. The volatile storage circuit is suitable for volatile storage of data. For example, the volatile storage circuit may include a random access memory (RAM) or similar volatile storage media. The non-volatile storage circuit is suitable for non-volatile storage of data. For example, the non-volatile storage circuit may include a read only memory (ROM), a solid state disk (SSD), and/or traditional hard disk drive (HDD), or similar non-volatile storage media.

The processor 23 is coupled to the communication interface 21 and the storage circuit 22. The processor 23 is suitable for being responsible for the overall or partial operation of the control host 14. For example, the processor 23 may include a central processing unit (CPU), other programmable general-purpose or specific-purpose microprocessors, digital signal processors (DSPs), programmable controllers, application specific integrated circuits (ASICs), programmable logic devices (PLDs), other similar devices, or a combination of these devices.

Figure 3:
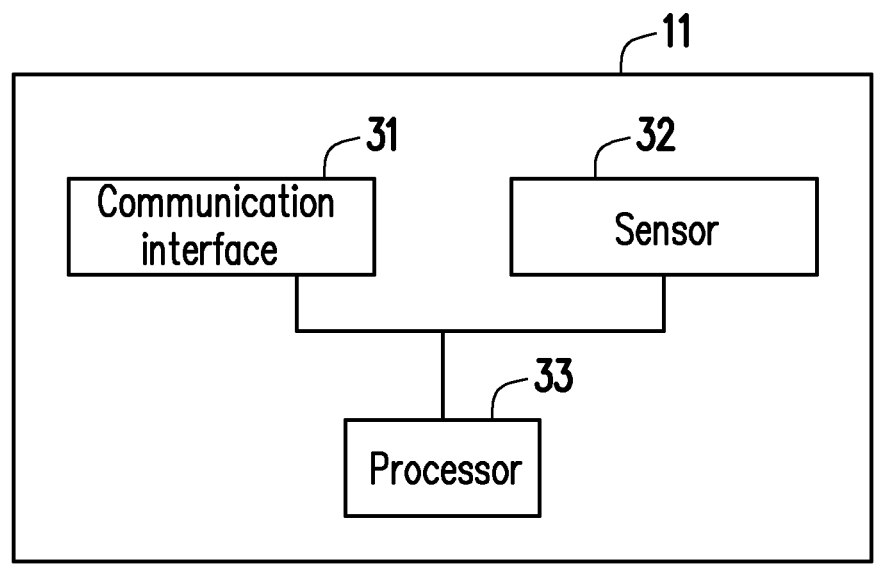
FIG. 3 is a schematic block diagram of a handheld guiding device according to an embodiment of the disclosure.

FIG. 3 is a schematic block diagram of a handheld guiding device according to an embodiment of the disclosure. Please refer to FIG. 3. The handheld guiding device 11 may include a communication interface 31, a sensor 32, and a processor 33. The communication interface 31 may include a communication circuit (such as a wired and/or wireless network card). For example, the communication interface 31 may support wireless communication protocols such as Wi-Fi, Bluetooth, BLE, or LTE, or wired communication protocols such as Ethernet.

The sensor 32 is disposed in the handheld guiding device 11. The sensor 32 is suitable for sensing the first physical motion of the handheld guiding device 11 and generating a first inertial measurement signal. In an embodiment, the first inertial measurement signal may reflect a moving direction, a tilting direction, a tilting angle, a pressing depth, and other measurement values related to the motion of the handheld guiding device 11 in the physical space when the handheld guiding device 11 executes the first physical motion. Therefore, in an embodiment, the sensor 32 may include various sensors that may generate inertial measurement signals, such as a gravity sensor, an acceleration sensor, a magnetic sensor, and/or a gyroscope. In addition, the number of the sensor 32 may be one or more, which is not limited thereto.

The processor 33 is coupled to the communication interface 31 and the sensor 32. The processor 23 is suitable for being responsible for the overall or partial operation of the handheld guiding device 11, such as sending the first inertial measurement signal to the control host 14 through the communication interface 31. The processor 23 may include a CPU, other programmable general-purpose or specific-purpose microprocessors, DSPs, programmable controllers, ASICs, PLDs, other similar devices, or a combination of these devices.

Figure 4:
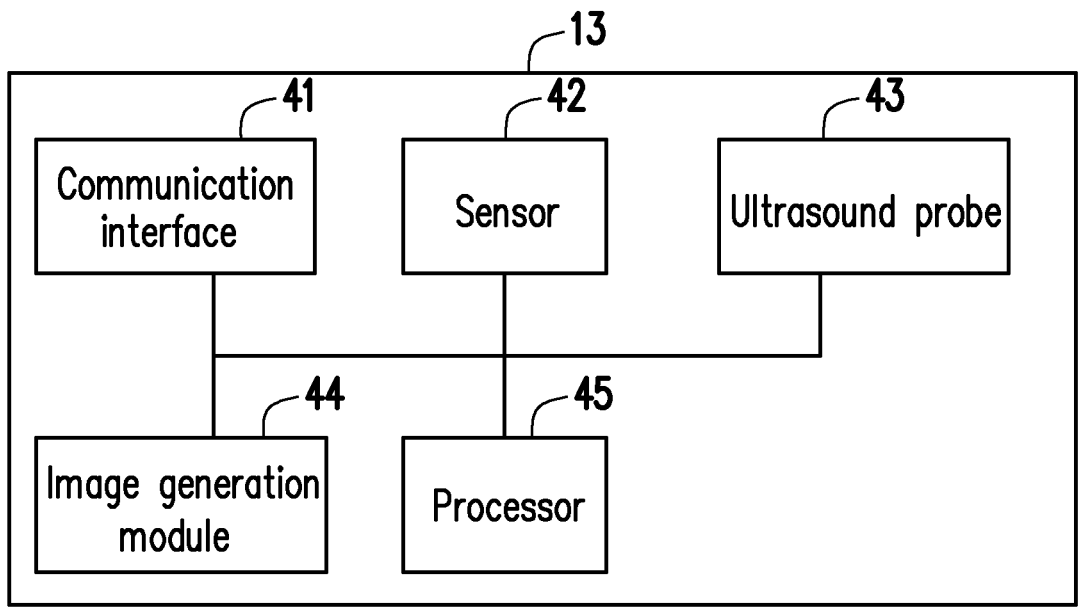
FIG. 4 is a schematic block diagram of an ultrasound scanning device according to an embodiment of the disclosure.

FIG. 4 is a schematic block diagram of an ultrasound scanning device according to an embodiment of the disclosure. Please refer to FIG. 4. The ultrasound scanning device 13 may include a communication interface 41, a sensor 42, an ultrasound probe 43, an image generation module 44, and a processor 45. The communication interface 41 may include a communication circuit containing a wired and/or wireless network card. For example, the communication interface 41 may support wireless communication protocols such as Wi-Fi, Bluetooth, BLE, or LTE, or wired communication protocols such as Ethernet.

The sensor 42 is disposed in the ultrasound scanning device 13. The sensor 42 is suitable for sensing the second physical motion of the ultrasound scanning device 13 and generating a second inertial measurement signal. In an embodiment, the second inertial measurement signal may reflect a moving direction, a tilting direction, a tilting angle, a pressing depth, and other measurement values related to the motion of the ultrasound scanning device 13 in the physical space when the ultrasound scanning device 13 executes the second physical motion. Therefore, in an embodiment, the sensor 42 may include various sensors that may generate inertial measurement signals, such as a gravity sensor, an acceleration sensor, a magnetic sensor, and/or a gyroscope. In addition, the number of the sensor 42 may be one or more, which is not limited thereto.

The ultrasound probe 43 is suitable for emitting an ultrasound signal to the contacted target 100 and receiving the ultrasound signal reflected by the target 100. The ultrasound signal reflected by the target 100 may carry internal structural information of the target 100.

The image generation module 44 is coupled to the ultrasound probe 43 and is suitable for generating the ultrasound image 102 according to the ultrasound signal reflected by the target 100. The ultrasound image 102 may reflect an internal structure of the target 100. The image generation module 44 may be implemented as software or hardware, which is not limited by the disclosure.

The processor 45 is coupled to the communication interface 41, the sensor 42, the ultrasound probe 43, and the image generation module 44. The processor 45 is suitable for the overall or partial operation of the ultrasound scanning device 13, such as sending the second inertial measurement signal and the ultrasound image 102 to the control host 14 through the communication interface 41. The processor 45 may include a CPU, other programmable general-purpose or specific-purpose microprocessors, DSPs, programmable controllers, ASICs, PLDs, other similar devices, or a combination of these devices.

In an embodiment, the sensor 32 of the handheld guiding device 11 may generate the first inertial measurement signal according to the first physical motion. The processor 33 of the handheld guiding device 11 may send the first inertial measurement signal to the control host 14 via the communication interface 31. The processor 23 of the control host 14 may receive the first inertial measurement signal via the communication interface 21 and analyze the first inertial measurement signal to obtain information related to the first physical motion. Based on the information, the processor 23 of the control host 14 may generate the navigation prompting information 101 and send the navigation prompting information 101 to the prompting device 15 via the communication interface 21 for presentation.

In an embodiment, the navigation prompting information 101 may reflect a moving trajectory of the handheld guiding device 11. For example, the moving trajectory may include at least one of the moving direction, the tilting direction, the tilting angle, and the pressing depth of the handheld guiding device 11. The operator at the operating end may operate the ultrasound scanning device 13 according to the navigation prompting information 101 to execute physical motions such as moving, tilting, and pressing along the moving trajectory of the handheld guiding device 11.

In an embodiment, the ultrasound scanning device 13 may include an optical emitter 131 and a main body 132. The optical emitter 131 may be disposed on the main body 132 as shown in FIG. 1. In an embodiment, the communication interface 41, the sensor 42, the ultrasound probe 43, and the image generation module 44 of FIG. 4 may be disposed in the main body 132.

In an embodiment, the control host 14 may send the navigation prompting information 101 to the processor 45 of the ultrasound scanning device 13. The processor 45 may control the optical emitter 131 to emit a light ray 103 according to the navigation prompting information 101 to guide the ultrasound scanning device 13 to move. The light ray 103 includes visible light and is suitable for guiding the ultrasound scanning device 13 to move. In an embodiment, the processor 45 may control the light ray 103 emitted by the optical emitter 131 to be directed toward a target direction according to the navigation prompting information 101 to guide the ultrasound scanning device 13 to move toward the target direction. In an embodiment, the light ray 103 and/or a light point formed by the light ray 103 irradiating on a certain object (such as the target 100) may also be regarded as partial information of the navigation prompting information 101. For example, the light ray 103 may project the moving trajectory guiding the ultrasound scanning device 13 on the target 100 according to the moving trajectory of the first physical motion, so that the operator of the ultrasound scanning device 13 may generate the second physical motion according to the guidance of the light ray 103. In addition, the main body 132 is suitable for providing the user of the ultrasound scanning device 13 to operate to capture the ultrasound image 102 and send the ultrasound image 102 to the control host 14.

The prompting device 15 is suitable for presenting the navigation prompting information 101. The navigation prompt information 101 is suitable for guiding the ultrasound scanning device 13 to execute the second physical motion according to the first physical motion. It should be noted that the prompting device 15 may contain one or more devices of the same or different types, and these devices may be disposed on the ultrasound scanning device 13 or independent of the ultrasound scanning device 13, which is not limited by the disclosure. In an embodiment, the optical emitter 131 may be one of the prompting devices 15.

In an embodiment, the prompting device 15 and the optical emitter 131 may co-exist in the guiding system for ultrasound scanning operation 10 to collaboratively operate. For example, in a situation where the prompting device 15 and the optical emitter 131 co-exist in the guiding system for ultrasound scanning operation 10, the optical emitter 131 may emit the light ray 103 to guide the ultrasound scanning device 13 to move. At the same time, the prompting device 15 may present at least part of the navigation prompting information 101, such as the moving trajectory or a moving directional index, to collaboratively guide the ultrasound scanning device 13. In another embodiment, the ultrasound scanning device 13 may not have the optical emitter 131.

In an embodiment, the control host 14 may detect the second physical motion of the ultrasound scanning device 13. For example, the sensor 42 of the ultrasound scanning device 13 may generate the second inertial measurement signal according to the second physical motion. The processor 45 of the ultrasound scanning device 13 may send the second inertial measurement signal to the control host 14 via the communication interface 41. The processor 23 of the control host 14 may receive the second inertial measurement signal via the communication interface 21 and analyze the second inertial measurement signal to obtain information related to the second physical motion.

In an embodiment, the control host 14 may compare the first physical motion and the second physical motion to obtain a difference between the first physical motion and the second physical motion. The difference may be reflected in the moving trajectory of the handheld guiding device 11 when executing the first physical motion and the moving trajectory of the ultrasound scanning device 13 when executing the second physical motion. In detail, the handheld guiding device 11 generates the first inertial measurement signal according to the first physical motion and sends the first inertial measurement signal to the control host 14. The ultrasound scanning device 13 generates the second inertial measurement signal according to the second physical motion and sends the second inertial measurement signal to the control host 14. Therefore, the control host 14 may judge whether the difference between the first physical motion and the second physical motion meets a warning condition according to the first inertial measurement signal and the second inertial measurement signal. In response to the difference between the first physical motion and the second physical motion meeting the warning condition, the control host 14 may instruct the prompting device 15 to output warning information. In addition, if the difference between the first physical motion and the second physical motion does not meet the warning condition, it means that the difference is within an allowable operating error range. The control host 14 may not instruct the prompting device 15 to output the warning information.

In an embodiment, the processor 23 of the control host 14 may compare the moving trajectory of the handheld guiding device 11 when executing the first physical motion and the motion trajectory of the ultrasound scanning device 13 when executing the second physical motion. In response to the difference between the moving trajectory of the handheld guiding device 11 when executing the first physical motion and the moving trajectory of the ultrasound scanning device 13 when executing the second physical motion exceeding an allowable value, the processor 23 may judge whether the difference between the first physical motion and the second physical motion meets the warning information and send a command message to the prompting device 15 via the communication interface 21. According to the command message, the prompting device 15 may output the warning information.

In an embodiment, the warning information may be presented on a display screen of the display via the prompting device 15. In an embodiment, the warning information may be conveyed via the sound-emitting device (such as the speaker or the buzzer) outputting a warning sound and/or the vibrating device (such as the vibrator) vibrating in the prompting device 15. For example, the sound-emitting device and/or the vibrating device may be disposed on the ultrasound scanning device 13 or independent of the ultrasound scanning device 13.

In an embodiment, the control host 14 may store the ultrasound image 102 captured by the ultrasound scanning device 13. For example, the ultrasound image 102 may be stored in the storage circuit 22 of the control host 14. However, in an embodiment, in response to the difference between the first physical motion and the second physical motion meeting the warning condition (such as the difference between the moving trajectory of the handheld guiding device 11 when executing the first physical motion and the moving trajectory of the ultrasound scanning device 13 when executing the second physical motion exceeding the allowable value), the control host 14 may discard the storage of the current ultrasound image 102 from the ultrasound scanning device 13. For example, when it is judged that the ultrasound image 102 may be discarded, the processor 23 of the control host 14 may not store the ultrasound image 102 in the storage circuit 22 or delete the ultrasound image 102 from the storage circuit 22. In this way, when the moving trajectory of the ultrasound scanning device 13 deviates too far from a preset trajectory (that is, the moving trajectory of the handheld guiding device 11), useless ultrasound images 102 occupying the storage space of the storage circuit 22 may be prevented from being continuously stored.

In an embodiment, in response to the difference between the first physical motion and the second physical motion meeting the warning condition, the control host 14 may instruct the prompting device 15 to present navigation correction information. The navigation correction information is suitable for correcting the moving trajectory of the ultrasound scanning device 13. For example, the navigation correction information may be presented on a screen displayed by the display of the prompting device 15. For example, the processor 23 of the control host 14 may send a command message to the prompting device 15 via the communication interface 21. According to the command message, the prompting device 15 may output the navigation correction information.

Figure 5:
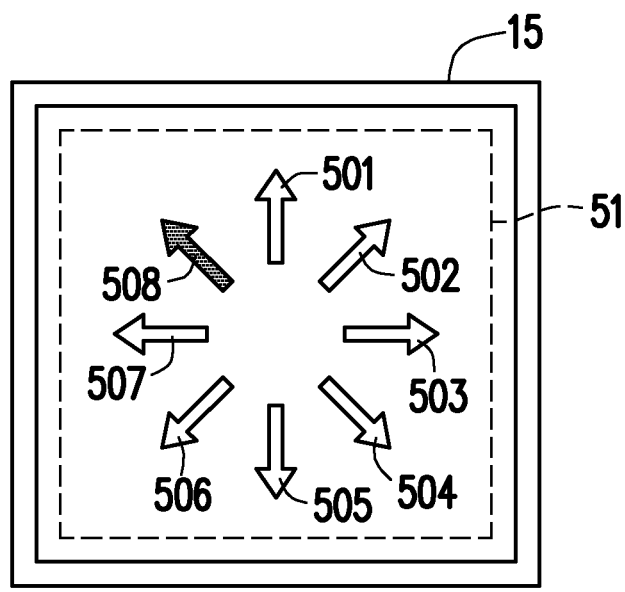
FIG. 5 is a schematic diagram of navigation correction information according to an embodiment of the disclosure.

FIG. 5 is a schematic diagram of navigation correction information according to an embodiment of the disclosure. Please refer to FIG. 5. In an embodiment, navigation correction information 51 may be presented on a screen displayed by the prompting device 15. The navigation correction information 51 may contain directional indexes 501 to 508 directed toward different directions. In an embodiment, one of the directional indexes 501 to 508 (such as the directional index 508) may change the visual effect (such as color change, magnification, or flicker) to clearly inform the operator of the ultrasound scanning device 13 that the current moving direction of the ultrasound scanning device 13 needs to move toward a specific direction (such as the direction directed by the directional index 508) to prevent the ultrasound scanning device 13 from continuously moving toward the wrong direction.

In an embodiment, the navigation correction information may also be presented via the light ray 103. For example, color or brightness features such as color, brightness, and flicker frequency of the light ray 103 may be changed according to the navigation correction information to warn the operator of the ultrasound scanning device 13 that the ultrasound scanning device 13 must move toward a specific direction or change the moving direction of the ultrasound scanning device 13.

Figure 6:
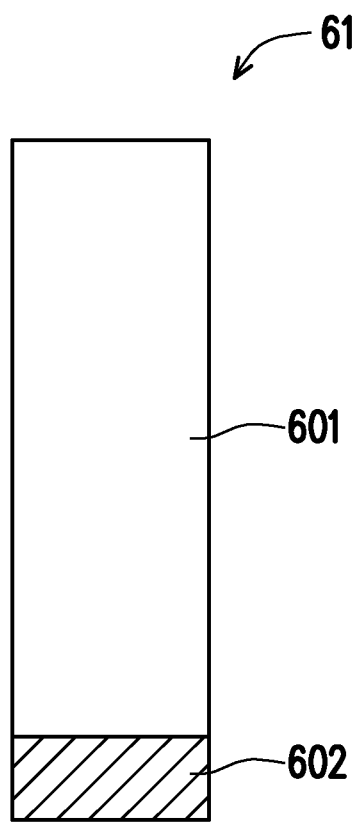
FIG. 6 is a schematic diagram of an appearance of a handheld guiding device according to an embodiment of the disclosure.

FIG. 6 is a schematic diagram of an appearance of a handheld guiding device according to an embodiment of the disclosure. Please refer to FIG. 6. In an embodiment, a handheld guiding device 61 may include a main body 601 and a soft material layer 602. The soft material layer 602 is disposed on the main body 601. It should be noted that the soft material layer 602 is implemented with a soft or elastic material (such as silicone). In addition, the main body 601 may be the same or similar to the handheld guiding device 11 of FIG. 1.

In an embodiment, when the operator of the handheld guiding device 61 operates the handheld guiding device 61 to execute the first physical motion to press the soft material layer 602 through the main body 601 to deform the soft material layer 602, the main body 601 may send the first inertial measurement signal generated by a sensor inside the main body 601 to the control host 14 according to the first physical motion. In this way, the control host 14 may obtain the moving trajectory (such as a distance, a depth, or a tilting angle of pressing toward the soft material layer 602) of the handheld guiding device 61 when executing the first physical motion according to the first inertial measurement signal and generate the corresponding navigation prompting information 101. Then, the control host 14 may use the navigation prompting information 101 to guide the operator of the ultrasound scanning device 13 to execute a similar second physical motion such as pressing or tilting.

Figure 7:
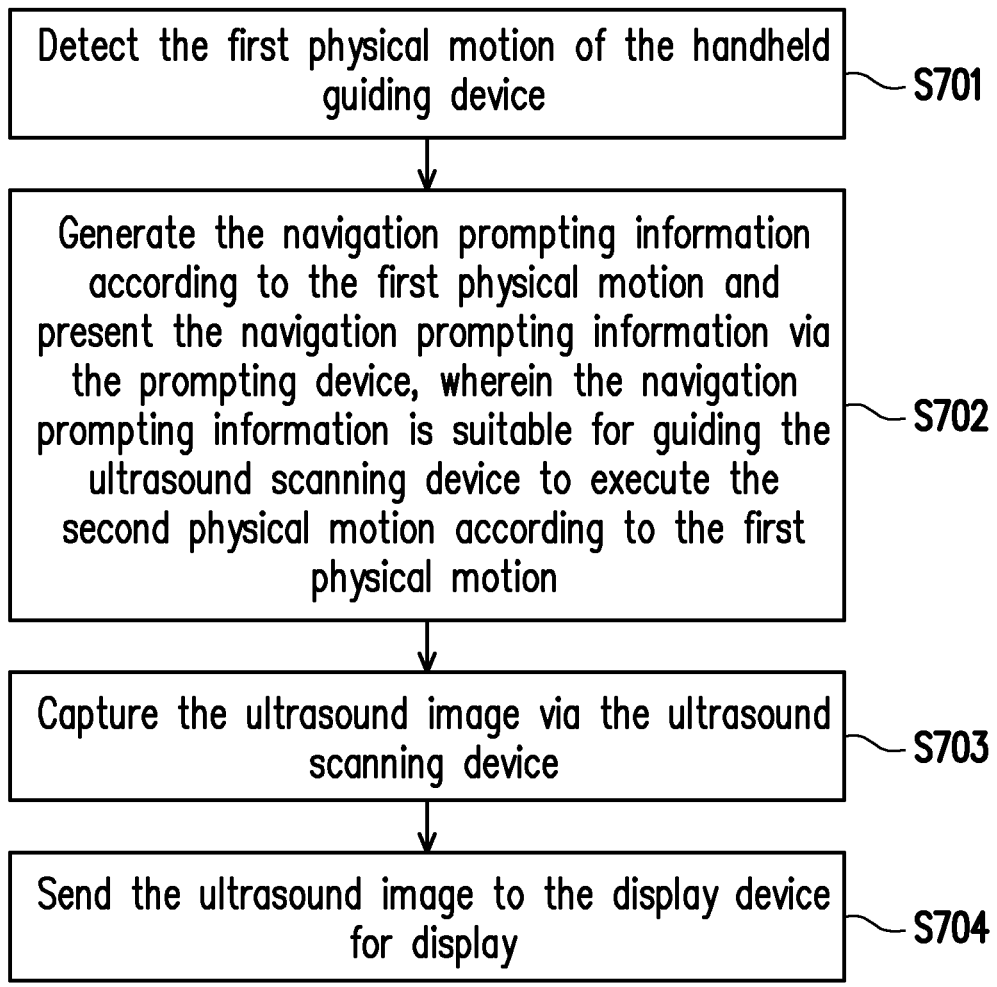
FIG. 7 is a flowchart of a guiding method for ultrasound scanning operation according to an embodiment of the disclosure.

FIG. 7 is a flowchart of a guiding method for ultrasound scanning operation according to an embodiment of the disclosure. Please refer to FIG. 7, which is executed by using the guiding system for ultrasound scanning operation 10. In Step S701, the first physical motion of the handheld guiding device is detected. In Step S702, the navigation prompting information is generated according to the first physical motion, and the navigation prompting information is presented via the prompting device. The navigation prompting information is suitable for guiding the ultrasound scanning device to execute the second physical motion according to the first physical motion. In Step S703, the ultrasound image is captured via the ultrasound scanning device. In Step S704, the ultrasound image is sent to the display device for display.

Figure 8:
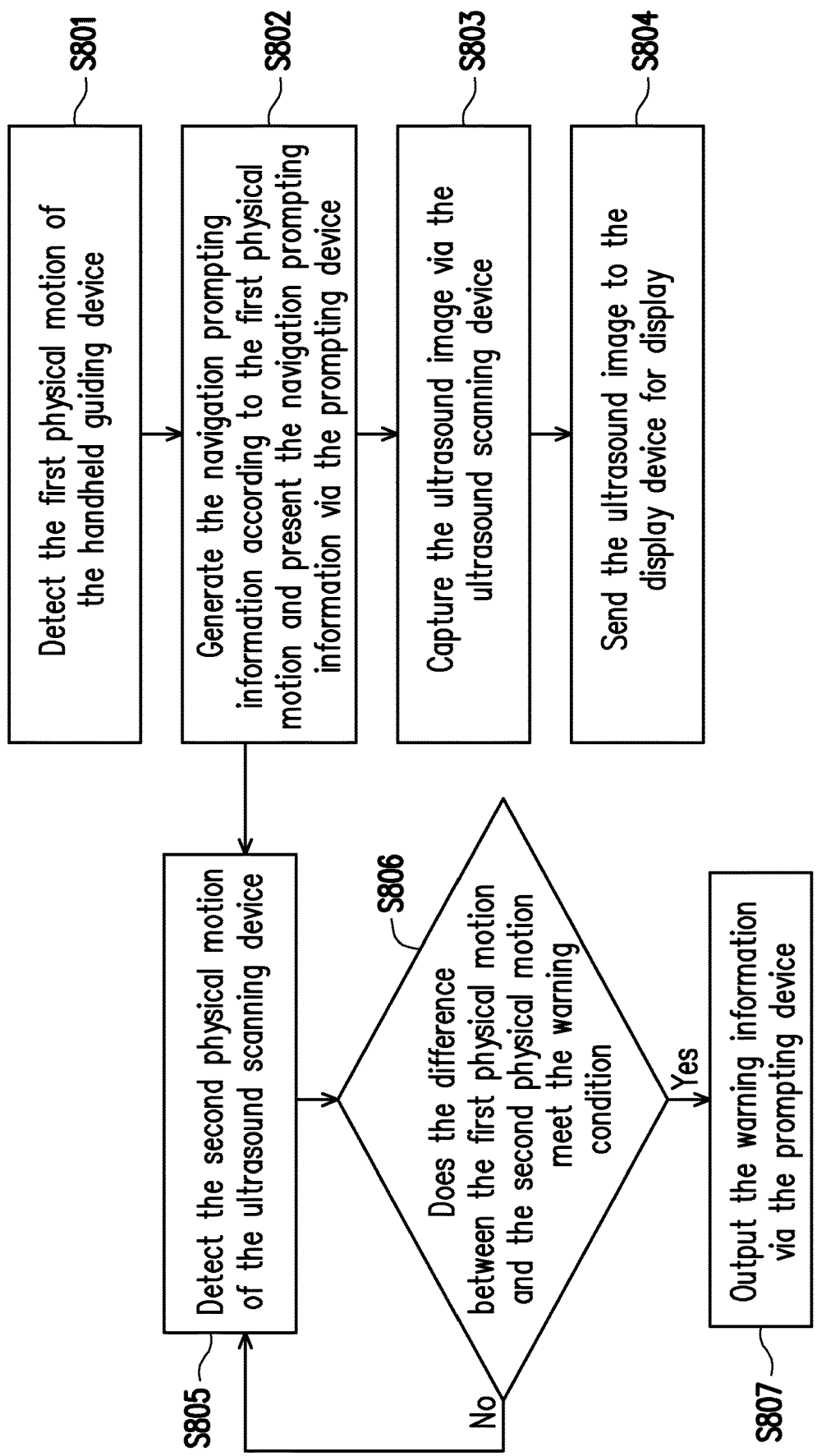
FIG. 8 is a flowchart of a guiding method for ultrasound scanning operation according to an embodiment of the disclosure.

FIG. 8 is a flowchart of a guiding method for ultrasound scanning operation according to an embodiment of the disclosure. Please refer to FIG. 8. In Step S801, the first physical motion of the handheld guiding device is detected. In Step S802, the navigation prompting information is generated according to the first physical motion, and the navigation prompting information is presented via the prompting device. The navigation prompting information is suitable for guiding the ultrasound scanning device to execute the second physical motion according to the first physical motion. In Step S803, the ultrasound image is captured via the ultrasound scanning device. In Step S804, the ultrasound image is sent to the display device for display. After executing the second physical motion, Step S805 is simultaneously performed with Step S803. In Step S805, the second physical motion of the ultrasound scanning device is detected. In Step S806, it is judged whether the difference between the first physical motion and the second physical motion meets the warning condition. If yes, in Step S807, the warning information is output via the prompting device. If not, return to Step S805. In addition, in an embodiment, Step S807 may also include discarding the currently captured ultrasound image when the warning condition is met.

However, each step in FIG. 7 and FIG. 8 has been described in detail as above and will not be repeated here. It is worth noting that each step in FIG. 7 and FIG. 8 may be implemented as multiple program codes or circuits, which is not limited by the disclosure. In addition, the methods of FIG. 7 and FIG. 8 may be used in conjunction with the above exemplary embodiments or may be used alone, which is not limited by the disclosure.

Based on the above, after detecting the first physical motion of the handheld guiding device, the navigation prompting information may be generated according to the first physical motion and presented via the prompting device. The navigation prompting information is suitable for guiding the ultrasound scanning device to execute the second physical motion according to the first physical motion. The ultrasound scanning device may continuously capture ultrasound images and send the captured ultrasound images to the display device for display. In this way, capturing efficiency of the ultrasound image in telemedicine can be improved.

In summary, through the interactive guiding operation between the handheld guiding device and the display device at the guiding end and the ultrasound scanning device and the prompting device at the operating end, even if the operator at the operating end is not familiar with the ultrasound scanning device, the operator at the operating end may still capture a suitable ultrasound image from the target according to the guidance of the instructor. In this way, capturing efficiency of the ultrasound image in telemedicine can be improved.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A guiding system for ultrasound scanning operation, comprising:
   a handheld electronic device, located at a guiding end;
   a display device, located at the guiding end;
   a handheld ultrasound scanner, located at an operating end;
   an information output hardware, located at the operating end;
   and a control host, communicatively connected between the guiding end and the operating end, wherein when the handheld electronic device generates a first physical motion, the control host generates navigation prompting information,
   the information output hardware is configured to present the navigation prompting information to guide the handheld ultrasound scanner to move to generate a second physical motion, and the control host captures an ultrasound image via the handheld ultrasound scanner and sends the ultrasound image to the display device at the guiding end for display,
   wherein the handheld electronic device comprises:

a main body;

a sensor;

and a soft material layer, disposed on the main body, wherein the sensor is configured to sense a first inertial measurement signal reflecting that the main body is pressing the soft material layer causing the soft material layer to be deformed and the main body sends the first inertial measurement signal to the control host according to the first physical motion of the handheld electronic device to reflect that the first physical motion contains the main body pressing the soft material layer and the navigation prompting information is generated according to the first inertial measurement signal.

2. The guiding system for ultrasound scanning operation according to claim 1, wherien the handheld electronic device further comprises:

a processor, coupled to the sensor and configured to send the first inertial measurement signal to the control host.

3. The guiding system for ultrasound scanning operation according to claim 1, wherein the handheld ultrasound scanner further comprises:

a second sensor for sensing the second physical motion of the handheld ultrasound scanner and generating a second inertial measurement signal;

an ultrasound probe for emitting an ultrasound signal to a target and receiving the ultrasound signal reflected by the target;

and a processor, coupled to the second sensor and the ultrasound probe, and the processor is configured to generate the ultrasound image according to the ultrasound signal reflected by the target and send the ultrasound image to the control host.

4. The guiding system for ultrasound scanning operation according to claim 1, wherein the handheld ultrasound scanner generates a second inertial measurement signal according to the second physical motion and sends the second inertial measurement signal to the control host, the control host judges whether a difference between the first physical motion and the second physical motion meets a warning condition according to the first inertial measurement signal and the second inertial measurement signal, and when the difference meets the warning condition, the control host instructs the information output hardware to output warning information.

5. The guiding system for ultrasound scanning operation according to claim 1, wherein in response to a difference between the first physical motion and the second physical motion meeting a warning condition, the control host instructs the information output hardware to output warning information.

6. The guiding system for ultrasound scanning operation according to claim 1, wherein the navigation prompting information is one of a moving trajectory or a moving directional index, and the moving trajectory comprises at least one of a moving direction, a tilting direction, a tilting angle, and a pressing depth.

7. The guiding system for ultrasound scanning operation according to claim 3, wherein the handheld ultrasound scanner further comprises:

a second main body for allowing a user to operate to capture the ultrasound image and to send the ultrasound image to the control host, wherein the second sensor, and the ultrasound probe are disposed in the second main body; wherein the information output hardware further comprises:

an optical emitter, disposed on the second main body, and wherein the processor controls the optical emitter to emit a light ray according to the navigation prompting information to guide the handheld ultrasound scanner to move.

8. The guiding system for ultrasound scanning operation according to claim 7, wherein the light ray is directed toward a target direction to guide the handheld ultrasound scanner to move toward the target direction.

9. The guiding system for ultrasound scanning operation according to claim 5, wherein in response to the difference meeting the warning condition, the control host further instructs the information output hardware to present navigation correction information for correcting a moving trajectory of the handheld ultrasound scanner.

10. A guiding method for ultrasound scanning operation, executed by using the guiding system for ultrasound scanning operation according to claim 1, comprising: sensing, via the sensor, the first inertial measurement signal; generating the navigation prompting information according to the first inertial measurement signal; presenting the navigation prompting information via the information output hardware; capturing the ultrasound image via the handheld ultrasound scanner; and sending the ultrasound image to the display device for display.

11. The guiding method for ultrasound scanning operation according to claim 10, further comprising:

Detecting the second physical motion of the handheld ultrasound scanner; and

Judging whether a difference between the first physical motion and the second physical motion meets a warning condition, and in response to the difference meeting the warning condition, outputting warning information via the information output hardware.

12. The guiding method for ultrasound scanning operation according to claim 11, further comprising:

Discarding the ultrasound image when the difference meets the warning condition.

* * * * *